United States Patent [19]

Sih

[11] 4,275,008
[45] Jun. 23, 1981

[54] 19-HYDROXY-19-METHYL-7a-HOMO-PGI₂ COMPOUNDS

[75] Inventor: John C. Sih, Portage, Mich.

[73] Assignee: The Upjohn Company, Kalamazoo, Mich.

[21] Appl. No.: 126,501

[22] Filed: Mar. 3, 1980

Related U.S. Application Data

[62] Division of Ser. No. 54,720, Jul. 5, 1979, Pat. No. 4,225,507.

[51] Int. Cl.³ ............................................. C07D 311/94
[52] U.S. Cl. ................................. 260/345.2; 542/431; 542/426; 542/422; 542/416; 542/421; 548/252; 548/253

[58] Field of Search ................... 260/345.2; 542/416, 542/421, 422, 426, 431; 548/252, 253

[56] References Cited

U.S. PATENT DOCUMENTS

4,123,441   10/1978   Johnson ........................... 260/345.2

*Primary Examiner*—Nicky Chan
*Attorney, Agent, or Firm*—Robert A. Armitage

[57] ABSTRACT

The present invention provides novel 19-hydroxy-19-methyl-7a-homo-PGI₂ compounds which are useful for pharmacological purposes, e.g., anti-asthmatic indications.

7 Claims, No Drawings

19-HYDROXY-19-METHYL-7a-HOMO-PGI$_2$ COMPOUNDS

CROSS REFERENCE TO RELATED APPLICATION

The present invention is a divisional application of U.S. Ser. No. 054,720, filed July 5, 1979, now U.S. Pat. No. 4,225,507.

BACKGROUND OF THE INVENTION

The present invention provides novel prostacyclin analogs. Particularly, the present invention relates to prostacyclin analogs substituted at the C-19 position by hydroxy.

Particularly, the present invention relates to 19-hydroxy-19-methyl-7a-homo-PGI$_2$ compounds. The novel prostacyclin analogs are useful for pharmacological purposes, e.g., as anti-asthmatic agents. The preparation and use of these compounds is incorporated here by reference from U.S. Pat. No. 4,225,507.

PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI$_2$, see R. A. Johnson, et al., Prostaglandins 15, 737–740 (1978).

SUMMARY OF THE INVENTION

The present invention particularly provides a prostacyclin-type compound of the formula

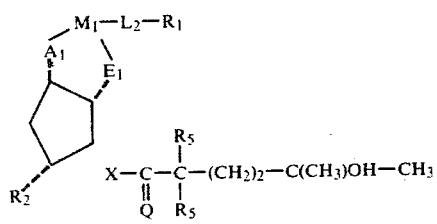

wherein A$_1$ is —O— (oxa) and E$_1$ is —CH$_2$CH$_2$—;
wherein L$_2$ is
(1) —(CH$_2$)$_j$—, wherein j is one to 4, inclusive,
(2) —(CH$_2$)$_q$—CF$_2$—, wherein q is one, 2, or 3; or
(3) —CH=CH—;
wherein M$_1$ is

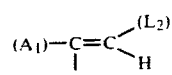

or

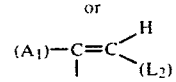

wherein Q is oxo, α—H:β—H, α—OH:β—R$_4$, or α—R$_4$:β—OH,
wherein R$_4$ is hydrogen or alkyl of one to 4 carbon atoms, inclusive,
wherein R$_1$ is
(1) —COOR$_3$,
(2) —CH$_2$OH,
(3) —CH$_2$N(R$_7$)(R$_8$),
(4) —CO—N(R$_7$)(R$_8$),
(5) —CO—NH—SO$_2$—R$_{15}$, or
(6) tetrazolyl,
wherein R$_3$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive;
(g) —(Ph)—CO—CH$_3$,
(h) —(p—Ph)—NH—CO—(p—Ph)—NH—CO—CH$_3$,
(i) —(p—Ph)—NH—CO—(p—Ph),
(j) —(p—Ph)—NH—CO—CH$_3$,
(k) —(p—Ph)—NH—CO—NH$_2$,
(l) —(p—Ph)—CH=N—NH—CO—NH$_2$,
(m) β-naphthyl,
(n) —CH$_2$—CO—R$_{16}$,
wherein —(Ph)— is inter-phenylene and —(p—Ph) is inter-para-phenylene or para-phenyl;
wherein R$_{16}$ is phenyl, p-bromophenyl, p-biphenylyl, p-nitrophenyl, p-benzamidophenyl, or 2-naphthyl, or
(o) a pharmacologically acceptable cation; wherein R$_7$ and R$_8$ are hydrogen, alkyl of one to 12 carbon atoms, inclusive, benzyl, or phenyl, being the same or different, and wherein R$_{15}$ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of 2 to 4 carbon atoms, inclusive,
wherein R$_2$ is hydrogen, hydroxyl, or hydroxymethyl,
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro, and
wherein X is
(1) trans—CH=CH—,
(2) cis—CH=CH—,
(3) —C≡C—, or
(4) —CH$_2$CH$_2$—,

I claim:
1. A prostacyclin-type compound of the formula

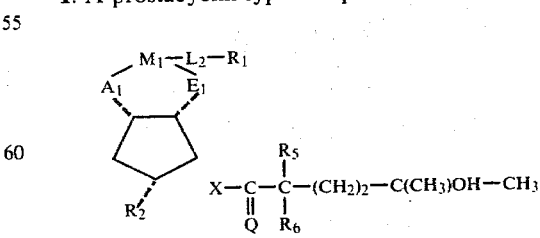

wherein A$_1$ is —O— (oxa) and E$_1$ is —CH$_2$CH$_2$—;
wherein L$_2$ is
(1) —(CH$_2$)$_j$—, wherein j is one to 4, inclusive,
(2) —(CH$_2$)$_q$—CF$_2$—, wherein q is one, 2, or 3, or (3) —CH=CH—;
wherein $M_1$ is

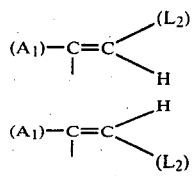

wherein Q is oxo, α—H:β—H, α—OH:β—$R_4$, or α—$R_4$:β—OH,
wherein $R_4$ is hydrogen or alkyl of one to 4 carbon atoms, inclusive,
wherein $R_1$ is
(1) —$COOR_3$,
(2) —$CH_2OH$,
(3) —$CH_2N(R_7)(R_8)$,
(4) —CO—$N(R_7)(R_8)$,
(5) —CO—NH—$SO_2$—$R_{15}$, or
(6) tetrazolyl,
wherein $R_3$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive;
(g) —(Ph)—CO—$CH_3$,
(h) —(p—Ph)—NH—CO—(p—Ph)—NH—CO—$CH_3$,
(i) —(p—Ph)—NH—CO—(p—Ph),
(j) —(p—Ph)—NH—CO—$CH_3$,
(k) —(p—Ph)—NH—CO—$NH_2$,
(l) —(p—Ph)—CH=N—NH—CO—$NH_2$,
(m) β-naphthyl,
(n) —$CH_2$—CO—$R_{16}$,
wherein —(Ph)— is inter-phenylene and —(p—Ph) is inter-paraphenylene or para-phenyl;

wherein $R_{16}$ is phenyl, p-bromophenyl, p-biphenylyl, p-nitrophenyl, p-benzamidophenyl, or 2-naphthyl, or
(o) a pharmacologically acceptable cation;
wherein $R_7$ and $R_8$ are hydrogen, alkyl of one to 12 carbon atoms, inclusive, benzyl, or phenyl, being the same or different, and wherein $R_{15}$ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of 2 to 4 carbon atoms, inclusive,
wherein $R_2$ is hydrogen, hydroxyl, or hydroxymethyl,
wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro, and
wherein X is
(1) trans—CH=CH—,
(2) cis—CH=CH—,
(3) —C≡C—, or
(4) —$CH_2CH_2$—.

2. A compound according to claim 1, wherein $R_1$ is —$CH_2OH$.

3. A compound according to claim 2, wherein $M_1$ is

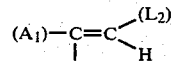

with bonds to $A_1$ and $L_2$ as shown.

4. A compound according to claim 3, wherein $L_2$ is —$(CH_2)_2$—.

5. A compound according to claim 4, wherein Q is α—OH:β—H, $R_2$ is hydroxyl, and X is trans—CH=CH—.

6. A compound according to claim 3, wherein $L_2$ is —CH=CH—.

7. A compound according to claim 6, wherein Q is α—OH:β—H, $R_2$ is hydroxy, and X is trans—CH=CH—.

* * * * *

UNITED STATES PATENT OFFICE
CERTIFICATE OF CORRECTION

Patent No. 4,275,008  Dated 23 June 1981

Inventor(s) John C. Sih

It is certified that error appears in the above-identified patent and that said Letters Patent are hereby corrected as shown below:

Column 1, lines 43-52, and column 2, lines 55-64, that portion of the formula reading should read

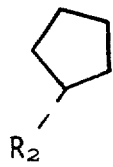 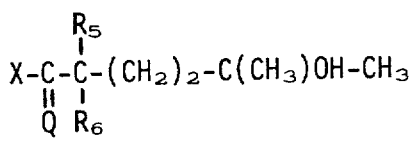  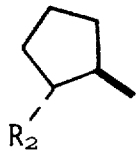 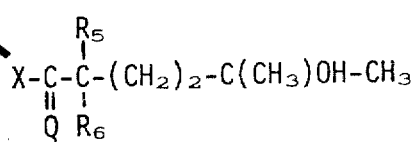

Signed and Sealed this

Eighth Day of September 1981

[SEAL]

Attest:

GERALD J. MOSSINGHOFF

Attesting Officer  Commissioner of Patents and Trademarks